United States Patent
Lee

(10) Patent No.: US 10,925,494 B2
(45) Date of Patent: Feb. 23, 2021

(54) OPTICAL SENSOR-BASED BLOOD PRESSURE MEASURING DEVICE

(71) Applicant: CHARMCARE CO., LTD., Seoul (KR)

(72) Inventor: Dong Hwa Lee, Yongin-si (KR)

(73) Assignee: CHARMCARE CO., LTD., Seoul (KR)

( * ) Notice: Subject to any disclaimer, the term of this patent is extended or adjusted under 35 U.S.C. 154(b) by 750 days.

(21) Appl. No.: 15/816,777

(22) Filed: Nov. 17, 2017

(65) Prior Publication Data

US 2019/0059750 A1  Feb. 28, 2019

(30) Foreign Application Priority Data

Aug. 25, 2017 (KR) .................. 10-2017-0108192

(51) Int. Cl.
  *A61B 5/021* (2006.01)
  *A61B 5/00* (2006.01)
  *A61B 5/024* (2006.01)

(52) U.S. Cl.
  CPC ...... *A61B 5/02108* (2013.01); *A61B 5/02116* (2013.01); *A61B 5/6824* (2013.01); *A61B 5/7278* (2013.01); *A61B 5/02427* (2013.01); *A61B 5/681* (2013.01); *A61B 2560/0247* (2013.01); *A61B 2562/0219* (2013.01); *A61B 2562/0233* (2013.01)

(58) Field of Classification Search
  None
  See application file for complete search history.

(56) References Cited

U.S. PATENT DOCUMENTS

2010/0125212 A1* 5/2010 Kim ............... A61B 5/022 600/485
2017/0172431 A1* 6/2017 Kim ............... A61B 5/02125

FOREIGN PATENT DOCUMENTS

| JP | 2001-275998 A | 10/2001 |
|---|---|---|
| KR | 2003-0061290 A | 7/2003 |
| KR | 10-2010-0024118 A | 3/2010 |
| KR | 10-2010-0116880 A | 11/2010 |
| KR | 10-2010-0119868 A | 11/2010 |
| KR | 10-2016-0028303 A | 3/2016 |
| KR | 10-2017-0073051 A | 6/2017 |

OTHER PUBLICATIONS

International Search Report dated Feb. 27, 2018 in corresponding International Patent Application No. PCT/KR2017/013050 (3 pages in Korean).

* cited by examiner

*Primary Examiner* — Pascal M Bui Pho
*Assistant Examiner* — Marjan Saboktakin
(74) *Attorney, Agent, or Firm* — NSIP Law

(57) ABSTRACT

A blood pressure measuring device according to the present disclosure includes: a light emitting element, a light receiving element, and a signal processing module configured to calculate a blood pressure value on the basis of a signal reflected to the light receiving element. Herein, the signal processing module generates an optical arterial pulse on the basis of the signal reflected to the light receiving element by executing a blood pressure measuring program and calculates a blood pressure value on the basis of the optical arterial pulse.

9 Claims, 6 Drawing Sheets

$\Delta P = g\, \rho\, \Delta h$ (p=BLOOD PRESSURE DIFFERENCE, g=ACCELERATION OF GRAVITY, $\rho$=BLOOD DENSITY, h=HEIGHT DIFFERENCE)

OPTICAL SENSOR-BASED BLOOD PRESSURE MEASURING DEVICE

CROSS-REFERENCE TO RELATED APPLICATION

This application claims the benefit under 35 USC 119(a) of Korean Patent Application No. 10-2017-0108192 filed on Aug. 25, 2017, in the Korean Intellectual Property Office, the entire disclosures of which are incorporated herein by reference for all purposes.

TECHNICAL FIELD

The present disclosure relates to an optical sensor-based blood pressure measuring device.

BACKGROUND

Recently, interest in health care has risen and the number of hypertensive patients and hypotensive patients has increased. Accordingly, studies on a wearable device that enables a user to easily check his/her blood pressure have been actively conducted.

Particularly, wearable devices configured to measure blood using an optical sensor instead of an air pump to improve the portability of a blood pressure measuring device are being developed. In such a blood pressure measuring device using an optical sensor, a light emitting element irradiates an optical signal to an object, a light receiving element senses a signal reflected from the object, and a signal processing module calculates a blood pressure value.

However, the conventional blood pressure measuring device cannot consider a blood pressure variation caused by the height of measurement and thus cannot measure an accurate blood pressure value.

PRIOR ART DOCUMENT

Korean Patent Laid-open Publication No. 10-2016-0028303 (entitled "Apparatus and method for monitoring blood pressure, wearable device having function of blood pressure monitoring")

SUMMARY

In view of the foregoing, the present disclosure provides a more accurate blood pressure value by calculating a difference in blood pressure and a difference in magnitude of optical arterial pulse signal between two points at different heights to set a magnitude of blood pressure per unit length, measuring a distance to the two points from a position of a baseline for an optical arterial pulse signal previously stored in a portable blood pressure measuring device on the basis of the magnitude of blood pressure per unit length, and applying the measured distance to a blood pressure value.

However, problems to be solved by the present disclosure are not limited to the above-described problems. There may be other problems to be solved by the present disclosure.

According to a first aspect of the present disclosure, a blood pressure measuring device includes: a light emitting element configured to irradiate an optical signal to a region of interest on an object; a light receiving element configured to sense a signal reflected from the region of interest; and a signal processing module configured to calculate a blood pressure value on the basis of the reflected signal. The signal processing module includes a memory in which a blood pressure measuring program is stored and a processor that executes the blood pressure measuring program. The program is executed by the processor to generate an optical arterial pulse on the basis of the reflected signal and calculate a blood pressure value on the basis of the optical arterial pulse. The blood pressure measuring device performs: a process of calculating a difference in blood pressure between a first point and a second point on the basis of a difference between a height of the portable blood pressure measuring device at the first point and a height of the portable blood pressure measuring device at the second point; a process of checking a magnitude of blood pressure per unit length by dividing a difference in signal magnitude between a first optical arterial pulse sensed at the first point and a second optical arterial pulse sensed at the second point by the calculated difference in blood pressure; and a process of calculating a distance to the first optical arterial pulse or the second optical arterial pulse from a position of a baseline for an optical arterial pulse signal previously stored in the portable blood pressure measuring device on the basis of the magnitude of blood pressure per unit length and calculating a blood pressure value of the first optical arterial pulse or a blood pressure value of the second optical arterial pulse.

According to a second aspect of the present disclosure, a blood pressure measuring device includes: a light emitting element configured to irradiate an optical signal to a region of interest on an object; a light receiving element configured to sense a signal reflected from the region of interest; and a signal processing module configured to calculate a blood pressure value on the basis of the reflected signal. The signal processing module includes a memory in which a blood pressure measuring program is stored and a processor that executes the blood pressure measuring program. The program is executed by the processor to generate an optical arterial pulse on the basis of the reflected signal and calculate a blood pressure value on the basis of the optical arterial pulse. The memory stores a reference height difference indicating a height difference between a position of a user's heart and a lowest position of the portable blood pressure measuring device worn on the user, and includes: a process of calculating a difference in height of measurement indicating a difference between a height of the portable blood pressure measuring device at a time of measuring a blood pressure of the user and a height of the lowest position; a process of calculating a compensation blood pressure on the basis of a value obtained by deducting the difference in height of measurement from the reference height difference; and a process of calculating a blood pressure value at the position of the heart at the time of measurement by adding up a blood pressure value at the time of measurement and the compensation blood pressure.

According to a third aspect of the present disclosure, a blood pressure measuring method uses a portable blood pressure measuring device that measures a blood pressure based on an optical sensor. The portable blood pressure measuring device: a process of calculating a difference in blood pressure between a first point and a second point on the basis of a difference between a height of the portable blood pressure measuring device at the first point and a height of the portable blood pressure measuring device at the second point; a process of checking a magnitude of blood pressure per unit length by dividing a difference in signal magnitude between a first optical arterial pulse sensed at the first point and a second optical arterial pulse sensed at the second point by the calculated difference in blood pressure; and a process of calculating a distance to the first optical arterial pulse or the second optical arterial pulse from a position of a baseline for an optical arterial pulse signal previously stored in the portable blood pressure measuring device on the basis of the magnitude of blood pressure per unit length and calculating a blood pressure value of the first optical arterial pulse or a blood pressure value of the second optical arterial pulse.

According to the above-described aspects of the present disclosure, it is possible to calculate a blood pressure with consideration of a blood pressure variation caused by the height of measurement and thus possible to calculate an accurate blood pressure value as compared with a conventional measuring method.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items.

DETAILED DESCRIPTION

Figure 1:
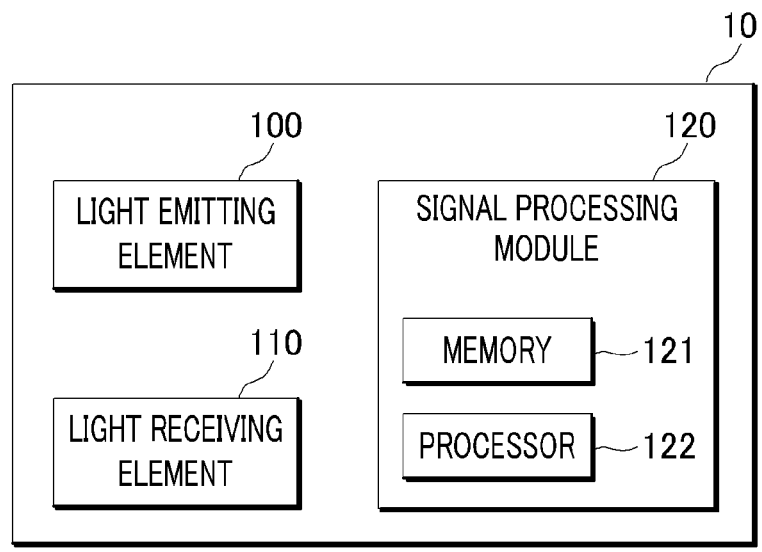
FIG. 1 is an example block diagram illustrating a configuration of an optical sensor-based blood pressure measuring device.

Hereinafter, embodiments of the present disclosure will be described in detail with reference to the accompanying drawings so that the present disclosure may be readily implemented by those skilled in the art. However, it is to be noted that the present disclosure is not limited to the embodiments but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element.

Through the whole document, the term "on" that is used to designate a position of one element with respect to another element includes both a case that the one element is adjacent to the other element and a case that any other element exists between these two elements.

Hereinafter, disclosed embodiments will be described in detail with reference to the accompanying drawings.

FIG. 1 is an example block diagram illustrating a configuration of an optical sensor-based blood pressure measuring device.

As illustrated in FIG. 1, an optical sensor-based blood pressure measuring device 10 includes a light emitting element 100, a light receiving element 110, and a signal processing module 120, and the signal processing module 120 includes a memory 121 in which a program for blood pressure measurement is stored and a processor 122 that executes the program.

The optical sensor-based blood pressure measuring device 10 is provided in the form of a wearable device to be worn on a user's wrist or the like and may have various forms such as a wrist watch, a smart band or a bracelet to be worn on a wrist. A detailed explanation of devices to be on a wrist will be omitted.

According to an operating principle of the present disclosure, the light emitting element 100 irradiates an optical signal such as a laser to a region of interest on an object and the light receiving element 110 senses a signal reflected from the region of interest and the signal processing module 120 calculates a blood pressure value on the basis of the reflected signal. Specifically, the blood pressure measuring program in the memory 121 included in the signal processing module 120 is executed by the processor 122, and the program is configured to generate an optical arterial pulse on the basis of the reflected signal and calculate a blood pressure value.

Herein, the light emitting element 100 may use an element such as a laser or the like and may be arranged to be irradiated toward the radial artery in the wrist, but is not necessarily limited thereto. The light emitting element 100 may be arranged to be irradiated toward other blood vessels around the wrist.

The light receiving element 110 is configured to receive a signal of the light emitting element 100 reflected from the region of interest. The signal of the light emitting element 100 received by the light receiving element 110 is transferred to the signal processing module 120. Herein, each of the light emitting element 100 and the light receiving element 110 employs a conventionally known configuration, and a detailed explanation thereof will be omitted.

The signal processing module 120 generates an optical arterial pulse on the basis of the signal of the light emitting element 100 received by the light receiving element 110 and calculates a blood pressure value on the basis of the optical arterial pulse.

The memory 121 stores the program for blood pressure measurement and various data required to execute the program. The memory 121 may collectively refer to a non-volatile storage device that retains information stored therein even when power is not supplied and a volatile storage device that requires power to retain information stored therein.

The processor 122 executes the program for blood pressure measurement stored in the memory 121 to perform a process of generating an optical arterial pulse and a process of calculating a blood pressure value. Particularly, in the present disclosure, blood pressures are measured from different points and a difference in blood pressure depending on difference in height of measurement is calculated. Then, a magnitude of blood pressure per unit length is calculated by dividing the difference in blood pressure by a difference in magnitude between optical arterial pulse signals to calculate an accurate blood pressure. In this case, the processor 122 may employ various micro computing processors generally available on the market.

Figure 5:
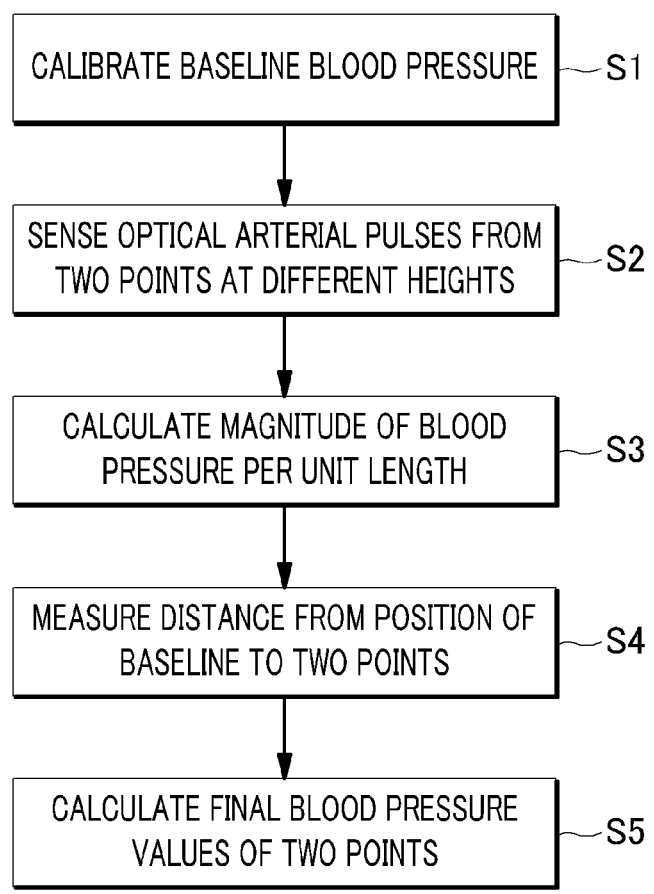
FIG. 5 is an example flowchart showing a blood pressure measuring method in consideration of a height difference.

FIG. 5 is an example flowchart showing a blood pressure measuring method in consideration of a height difference.

Firstly, a reference optical arterial pulse generated during a calibration process which is an initial setup process is matched in the program stored in the memory 121 and a reference blood pressure value input via measurement by an external manometer is matched with the reference optical arterial pulse to set a position of the baseline (S1). Through this process, a baseline indicating a value 0 on a Y-axis for an optical arterial pulse signal to be input later can be specified.

Figure 8:
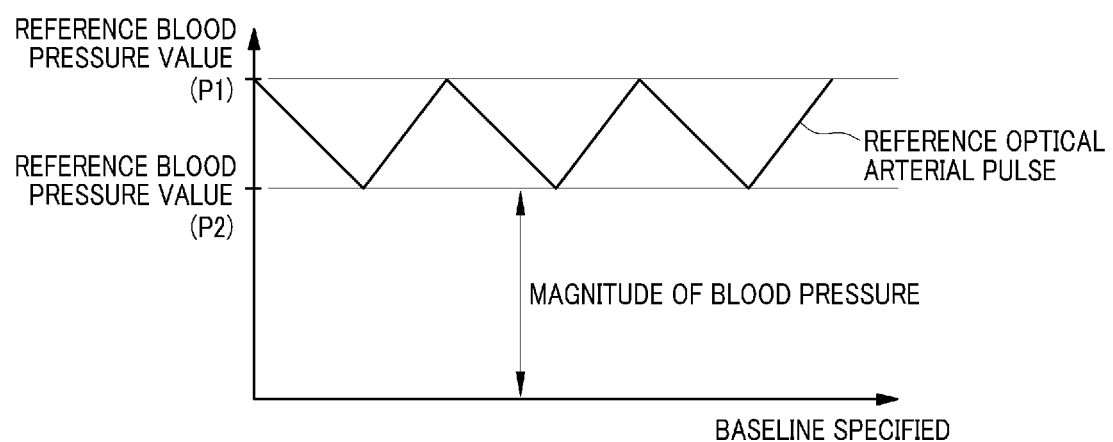
FIG. 8 is an example diagram provided to explain a process of setting a position of a baseline.

Referring to FIG. 8, if the reference blood pressure value is matched with the reference optical arterial pulse during the initial setup process, values (P1 and P2) on the Y-axis can be specified for the reference optical arterial pulse. If the values are traced back from the reference optical arterial pulse, a base line indicating a value 0 on the Y-axis can be specified.

Meanwhile, a specific method of generating an optical arterial pulse signal is conventionally known as disclosed in Korean Patent Laid-open Publication No. 10-2016-0028303 and the like. Therefore, a detailed explanation thereof will be omitted.

Then, optical arterial pulses are sensed from points at different heights (S2). In this case, the object's optical arterial pulses generated when the blood pressure measuring device 10 is positioned at a first point h1 and a second point h2 are sensed.

Figure 2:
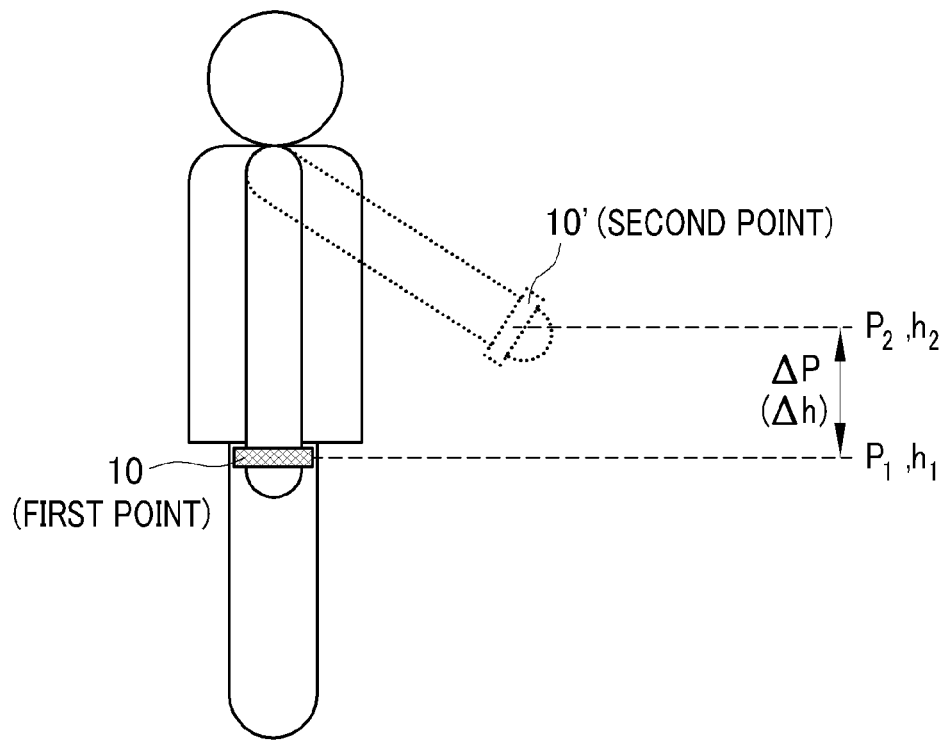
FIG. 2 is an example diagram provided to explain a process to be performed by a blood pressure measuring device.

FIG. 2 is an example diagram provided to explain a process to be performed by a blood pressure measuring device.

As illustrated in FIG. 2, while the blood pressure measuring device 10 is worn on the wrist, optical arterial pulses are generated at the first point h1 and the second point h2, respectively, and heights of measurement are also sensed. In this case, the blood pressure measuring device 10 may include one or more of an acceleration sensor, a gyro sensor, an altitude sensor, and a differential manometer, and a height of a point where the blood pressure measuring device 10 is positioned is calculated on the basis of sensing values output from one or more of the acceleration sensor, the gyro sensor, the altitude sensor, and the differential manometer.

Figures 3, 4:
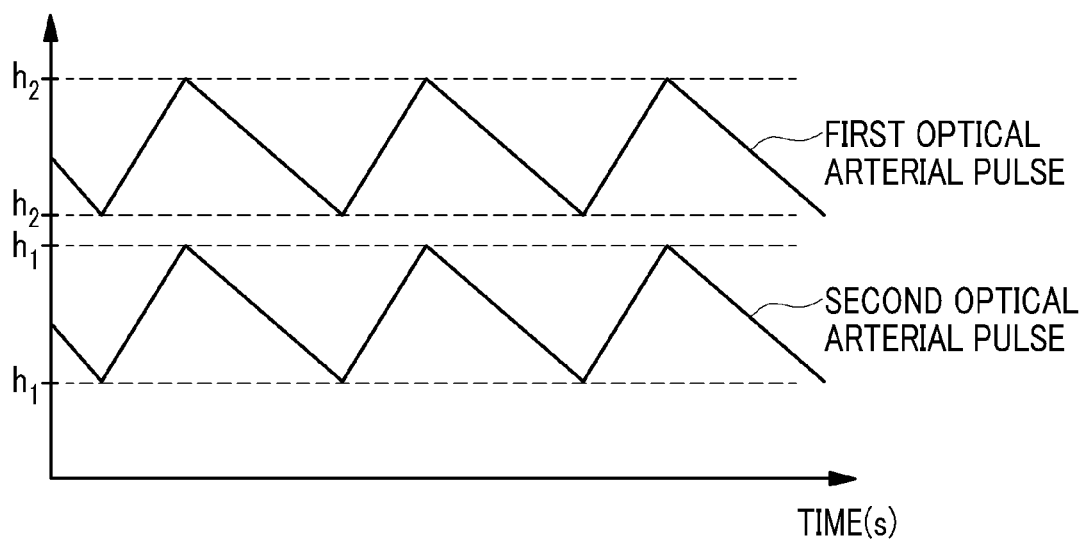
FIG. 3 is an optical arterial pulse signal graph provided to explain a blood pressure calculating method.
FIG. 4 is an equation for calculating a blood pressure difference.

As such, if a height of the first point h1 and a height of the second point h2 are sensed, a difference in blood pressure between the first point h1 and the second point h2 can be calculated according to an equation as shown in FIG. 4.

In this case, the acceleration of gravity is a fixed value and a blood density p may be a predetermined value stored in the blood pressure measuring device 10 or may be measured from each user and stored in the blood pressure measuring device 10.

Referring to FIG. 5 again, a magnitude of blood pressure per unit length is set by dividing a difference in signal magnitude between a first optical arterial pulse sensed at the first point h1 and a second optical arterial pulse sensed at the second point h2 by a blood pressure difference ΔP calculated in the above-described process S2 (S3). For example, the difference in signal magnitude may be calculated by subtracting a peak value of the first optical arterial pulse from a peak value of the second optical arterial pulse. In this case, the magnitude of blood pressure per unit length is a value to be used for blood pressure measurement on an optical arterial pulse signal graph and indicates a magnitude of blood pressure relative to a distance of an optical arterial pulse signal on the Y-axis. Therefore, after the magnitude of blood pressure per unit length is set, if a distance of an optical arterial pulse signal on the Y-axis is obtained, a blood pressure of the optical arterial pulse signal can be calculated.

Then, a distance to the first optical arterial pulse or the second optical arterial pulse from a position of the baseline for an optical arterial pulse signal previously stored in the portable blood pressure measuring device 10 is measured (S4).

Then, a blood pressure value is calculated by multiplying the measured distance by the magnitude of blood pressure per unit length (S5).

FIG. 3 is an optical arterial pulse signal graph provided to explain a blood pressure calculating method.

It is possible to calculate blood pressure values of the first optical arterial pulse sensed at the first point h1 and the second optical arterial pulse sensed at the second point h2, respectively, using the magnitude of blood pressure per unit length as calculated in the previous process S3.

As for the first optical arterial pulse, the baseline is set in the previous process S1. Therefore, a distance from the baseline to a lowest position of the first optical arterial pulse can be specified. Then, a blood pressure at the lowest position of the first optical arterial pulse can be calculated by multiplying the distance by the magnitude of blood pressure per unit length. Likewise, a distance from the baseline to a highest position of the first optical arterial pulse can be specified. Then, a blood pressure at the highest position of the first optical arterial pulse can be calculated by multiplying the distance by the magnitude of blood pressure per unit length.

Figure 7:
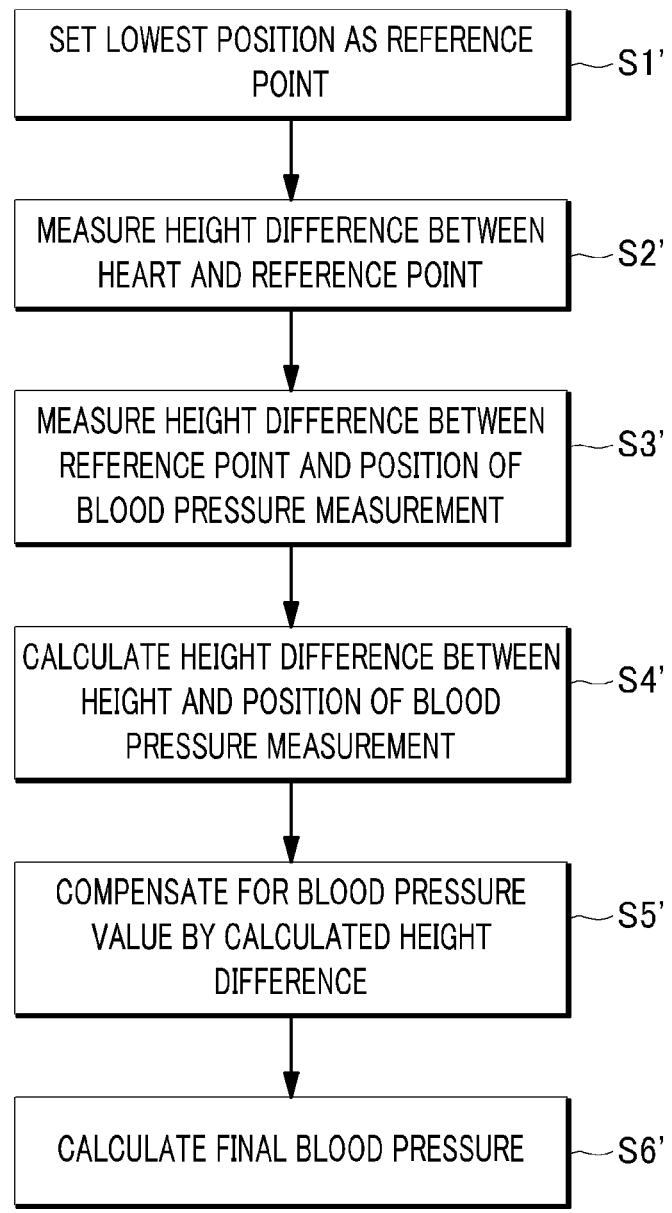
FIG. 7 is an example flowchart showing a blood pressure measuring method in consideration of a height difference between a lowest position of a blood pressure measuring device and a heart.

FIG. 7 is an example flowchart showing a blood pressure measuring method in consideration of a height difference between a lowest position of a blood pressure measuring device and a heart.

Hereinafter, a blood pressure measuring method in consideration of a height difference between a lowest position of a blood pressure measuring device and a heart will be described with reference to FIG. 7.

The present measuring method is based on the measuring method using the magnitude of blood pressure per unit length described above with reference to FIG. 5, and a detailed explanation thereof will be the same as described above.

Firstly, a lowest position (hereinafter, referred to as "first point") of the portable blood pressure measuring device 10 while the user wears the portable blood pressure measuring device 10 is set (S1'). Typically, the user wears the portable blood pressure measuring device 10 on the wrist, and, thus, the first point can be determined by an arm length of each user.

Figure 6:
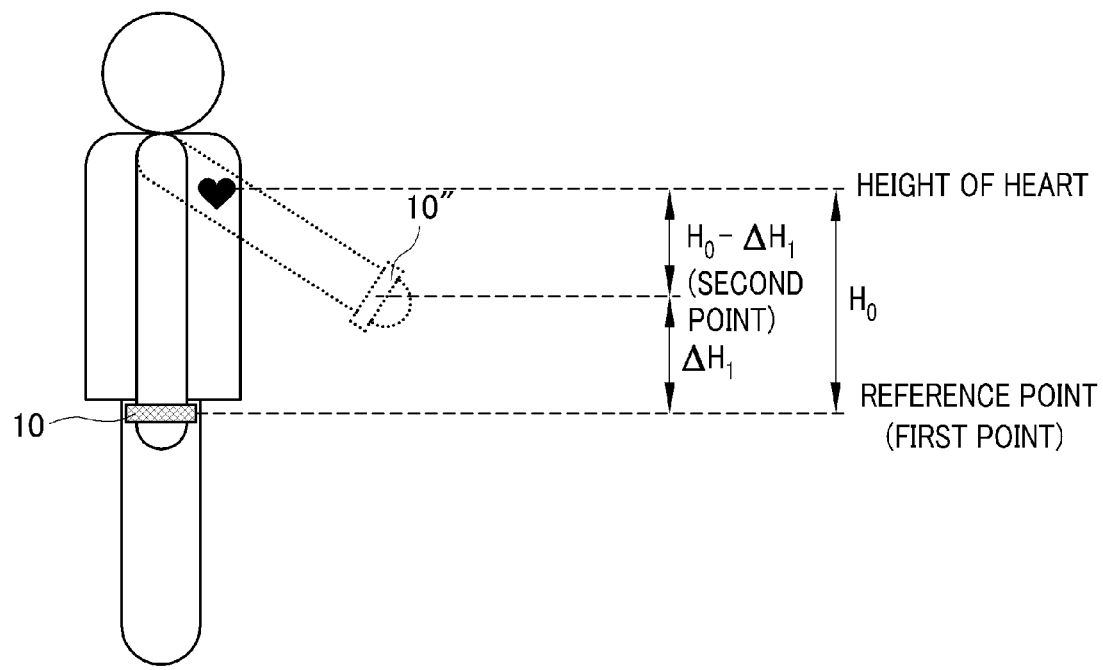
FIG. 6 is an example diagram provided to explain a height difference between a lowest position of a blood pressure measuring device and a heart.

Referring to FIG. 6, a distance H0 from the first point to the heart is measured (S2'). A height difference between the lowest position and a position of the heart can be measured using various sensors included in the portable blood pressure measuring device 10. However, the user may choose to measure the height difference using a tapeline and input and store the height difference in the portable blood pressure measuring device 10.

Then, a distance ΔH1 from the first point to a current position of blood pressure measurement (hereinafter, referred to as "second point") is measured (S3'). Herein, the current position of blood pressure measurement refers to a certain position between the position of the user's heart and the lowest position.

Then, a distance H0-ΔH1 from the second point to the heart is calculated by deducting the distance from the first point to the second point ΔH1 from the distance H0 from the first point to the heart is calculated (S4').

The calculated distance H0-ΔH1 from the second point to the heart is divided by the unit length and then multiplied by the magnitude of blood pressure per unit length calculated through the process described above with reference to FIG. 5. A resultant blood pressure value is compensated for a blood pressure value at the second point (S5') to calculate a final blood pressure value (S6'). That is, the blood pressure value at the second point is calculated by the method described above with reference to FIG. 5 and a compensation process is performed by adding up the blood pressure value and a value obtained by multiplying the distance H0-ΔH1 from the second point to the heart by the magnitude of blood pressure per unit length.

Through this process, a blood pressure measured at a certain point can be converted into a blood pressure value at a position of the heart.

The embodiment of the present disclosure can be embodied in a storage medium including instruction codes executable by a computer such as a program module executed by the computer. A computer-readable medium can be any usable medium which can be accessed by the computer and includes all volatile/non-volatile and removable/non-removable media. Further, the computer-readable medium may include all computer storage. The computer storage medium includes all volatile/non-volatile and removable/non-removable media embodied by a certain method or technology for storing information such as computer-readable instruction code, a data structure, a program module or other data.

The system and method of the present disclosure has been explained in relation to a specific embodiment, but its components or a part or all of its operations can be embodied by using a computer system having general-purpose hardware architecture.

The above description of the present disclosure is provided for the purpose of illustration, and it would be understood by those skilled in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

I claim:

1. A portable blood pressure measuring device that measures a blood pressure based on an optical sensor, comprising:
a light emitting element configured to irradiate an optical signal to a region of interest on an object;
a light receiving element configured to sense a signal reflected from the region of interest; and
a signal processing module configured to calculate a blood pressure value on the basis of the reflected signal,
wherein the signal processing module includes a non-transitory storage medium in which a blood pressure measuring program is stored and a processor that executes the blood pressure measuring program,
the blood pressure measuring program is executed by the processor to generate an optical arterial pulse on the basis of the reflected signal and calculate a blood pressure value on the basis of the optical arterial pulse, and
the signal processing module is configured to perform:
a process of calculating a difference in blood pressure between a first point and a second point on the basis of a difference between a height of the portable blood pressure measuring device at the first point and a height of the portable blood pressure measuring device at the second point;
a process of checking a magnitude of blood pressure per unit length by dividing a difference in signal magnitude between a first optical arterial pulse sensed at the first point and a second optical arterial pulse sensed at the second point by the calculated difference in blood pressure; and
a process of calculating a distance to the first optical arterial pulse or the second optical arterial pulse from a position of a baseline for an optical arterial pulse signal previously stored in the portable blood pressure measuring device on the basis of the magnitude of blood pressure per unit length and calculating a blood pressure value of the first optical arterial pulse or a blood pressure value of the second optical arterial pulse.

2. The portable blood pressure measuring device of claim 1,
wherein the signal processing module is configured to receive a reference blood pressure value input via measurement by an external manometer and matching with a reference optical arterial pulse generated during an initial setup process and set a position of the baseline by matching the reference blood pressure value with the reference optical arterial pulse.

3. The portable blood pressure measuring device of claim 1,
wherein the light emitting element is configured to output a laser,
the portable blood pressure measuring device includes one or more of an acceleration sensor, a gyro sensor, an altitude sensor, and a differential manometer, and
the signal processing module is configured to calculate a height of the portable blood pressure measuring device on the basis of sensing values output from one or more of the acceleration sensor, the gyro sensor, the altitude sensor, and the differential manometer.

4. The portable blood pressure measuring device of claim 1,
wherein the signal processing module is configured to calculate a distance from the baseline to a lowest position or a highest position of the optical arterial pulse and calculate the blood pressure value by multiplying the distance by the magnitude of blood pressure per unit length.

5. The portable blood pressure measuring device of claim 1,
wherein the signal processing module is configured to receive a reference blood pressure value input via measurement by an external manometer and matching with a reference optical arterial pulse generated during an initial setup process and set a position of the baseline by matching the reference blood pressure value with the reference optical arterial pulse, and
wherein the signal processing module is further configured to perform:

a process of calculating a difference in blood pressure between a first point and a second point on the basis of a difference between a height of the portable blood pressure measuring device at the first point and a height of the portable blood pressure measuring device at the second point;

a process of checking a magnitude of blood pressure per unit length by dividing a difference in signal magnitude between a first optical arterial pulse sensed at the first point and a second optical arterial pulse sensed at the second point by the calculated difference in blood pressure; and a process of calculating a distance from the baseline to a lowest position or a highest position of the optical arterial pulse and calculating a blood pressure value at the time of measurement by multiplying the distance by the magnitude of blood pressure per unit length.

6. A blood pressure measuring method using a portable blood pressure measuring device that measures a blood pressure based on an optical sensor, wherein the portable blood pressure measuring device performs:

a process of calculating a difference in blood pressure between a first point and a second point on the basis of a difference between a height of the portable blood pressure measuring device at the first point and a height of the portable blood pressure measuring device at the second point;

a process of checking a magnitude of blood pressure per unit length by dividing a difference in signal magnitude between a first optical arterial pulse sensed at the first point and a second optical arterial pulse sensed at the second point by the calculated difference in blood pressure; and a process of calculating a distance to the first optical arterial pulse or the second optical arterial pulse from a position of a baseline for an optical arterial pulse signal previously stored in the portable blood pressure measuring device on the basis of the magnitude of blood pressure per unit length and calculating a blood pressure value of the first optical arterial pulse or a blood pressure value of the second optical arterial pulse.

7. The blood pressure measuring method of claim 6, further comprising:

setting the position of the baseline for the optical arterial pulse signal by matching a reference optical arterial pulse with a reference blood pressure value input via measurement by an external manometer.

8. The blood pressure measuring method of claim 6, wherein the process of calculating a blood pressure value includes calculating a distance from the baseline to a lowest position or a highest position of the first optical arterial pulse or the second optical arterial pulse and calculating the blood pressure value by multiplying the distance by the magnitude of blood pressure per unit length.

9. The blood pressure measuring method of claim 6, further comprising:

a process of calculating a difference in height of measurement indicating a difference between a height of the portable blood pressure measuring device at the first point or the second point and a height of a lowest position of the portable blood pressure measuring device worn on a user;

a process of calculating a compensation blood pressure on the basis of a value obtained by deducting the difference in height of measurement from a reference height difference indicating a height difference between a position of the user's heart and the lowest position; and a process of calculating a blood pressure value for the position of the heart at the first point or the second point by adding up a blood pressure value of the first optical arterial pulse or a blood pressure value of the second optical arterial pulse and the compensation blood pressure.

* * * * *